United States Patent [19]

Mizuno et al.

[11] Patent Number: 4,477,159

[45] Date of Patent: Oct. 16, 1984

[54] PHOTOCOAGULATOR

[75] Inventors: Katsuyoshi Mizuno, Izumi; Akira Ihara, Gamagori, both of Japan

[73] Assignee: Nidek Co., Ltd., Aichi, Japan

[21] Appl. No.: 318,593

[22] Filed: Nov. 5, 1981

[30] Foreign Application Priority Data

Nov. 6, 1980 [JP] Japan .................. 55-156207
Jun. 30, 1981 [JP] Japan .................. 56-102691

[51] Int. Cl.³ .............................................. A61B 3/10
[52] U.S. Cl. ................................. 351/221; 351/205; 351/214
[58] Field of Search ............... 351/221, 214, 213, 205; 128/303.1, 395

[56] References Cited

U.S. PATENT DOCUMENTS 3,096,767  7/1963  Gressler et al. ............. 351/221 X
3,582,191  6/1971  Cohen et al. ............... 351/221 O
3,583,795  6/1971  Heine ......................... 351/221
3,703,176  11/1972 Vassiliadis et al. .......... 351/221 X
3,783,874  1/1974  Koester et al. .............. 351/221 X

OTHER PUBLICATIONS

Shimizu et al., "Photocoagulation", Aug. 1, 1977.

Primary Examiner—Rodney B. Bovernick
Attorney, Agent, or Firm—Armstrong, Nikaido, Marmelstein & Kubovcik

[57] ABSTRACT

A photocoagulator of the type having a light source device and an ophthalmoscope device. The light source device and the ophthalmoscope device are optically connected to each other by optical fiber means adapted to transmit the light.

4 Claims, 5 Drawing Figures

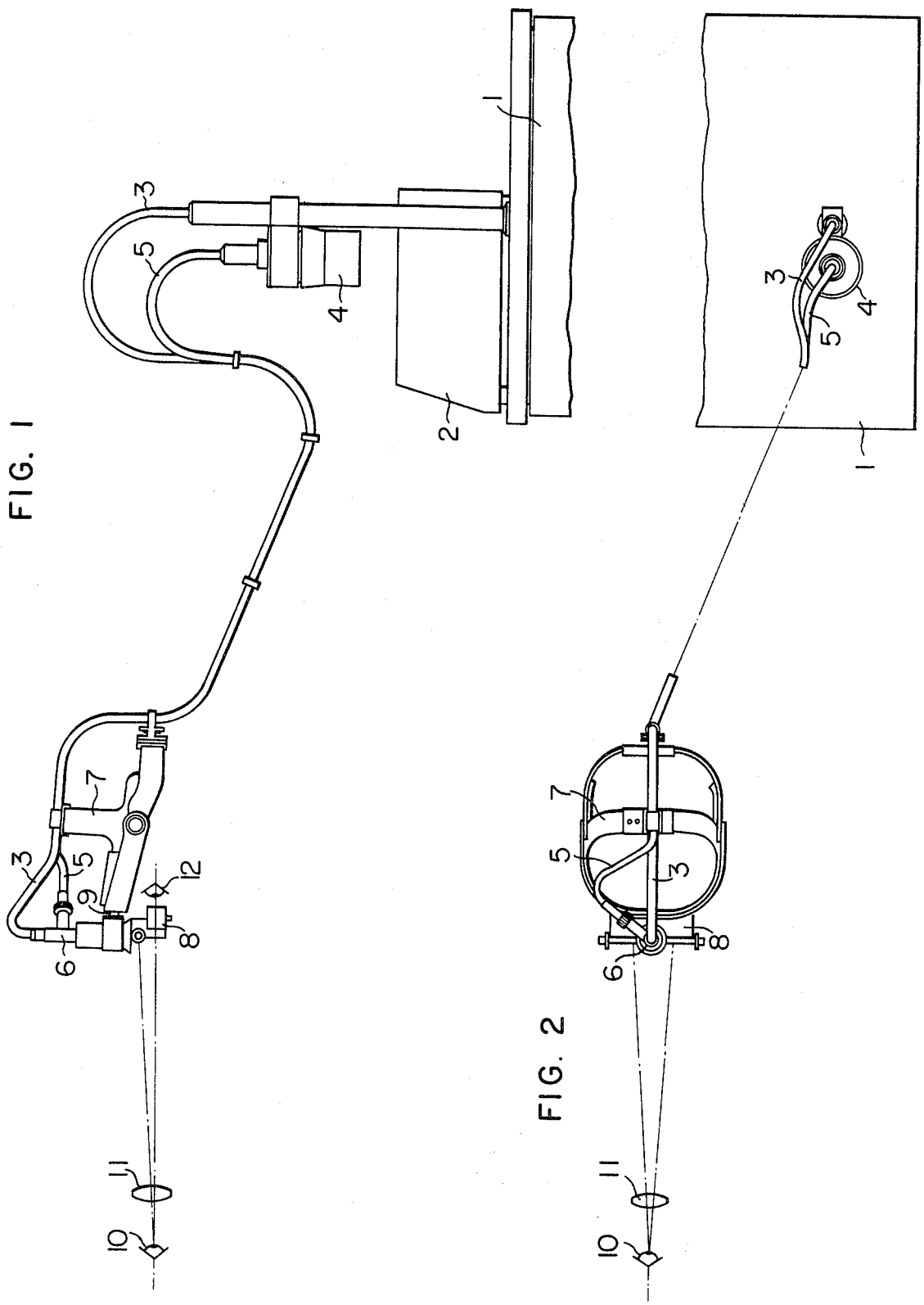

PHOTOCOAGULATOR

BACKGROUND OF THE INVENTION

The present invention relates to a photocoagulator and, more particularly, to a photocoagulator adapted to introduce a remedial light beam from a light source into an indirect opthalmoscope carried by the head, etc. of an operator and then, to apply the same coaxially with an illumination light for inspection to a patient's fundus oculi thereby to cure a defective part of the fundus oculi.

More specifically, the present invention relates to a photocoagulator in which the optical path of laser beam from a laser oscillator is arranged to be switchable between two optical fibers one of which transmits laser beam to an opthalmoscope and the other one of which transmits laser beam to a slit lamp, thereby the medical treatment of a patient's fundus oculi can be suitably made in accordance with positions of a lesion to be treated by selectively using the opthalmoscope and the slit lamp.

The photocoagulator has been widely used effectively for the remedy of various oculopathies such as retinal detachment, central serous retinopathy, retinal vein occlusion, diabetic retinopathy and so forth.

The photocoagulator is a device which is adapted to be used in combination with an ophthalmoscope so as to introduce, while the fundus oculi is inspected for detection of any lesion by means of an opthalmoscope, the remedial light beam to the lesion through the ophthalmoscope thereby to effect a photocoagulation.

Hitherto, various types of ophthalmoscopes have been used such as handy type monocle direct ophthalmoscope, handy type monocle indirect ophthalmoscope, binocular microscope, and combination of a slit-lamp and a contact lens.

The monocle direct and indirect ophthalmoscopes have a comparatively large degree of freedom of operation, but requires a high degree of skill and experience in the operation partly because of limited field of vision and partly because of the monocular structure.

The binocular microscope suffers disadvantage that the degree of freedom of movement of the binocular microscope is rather small, because the binocular microscope and the light source section are connected by means of a rigid arm mechanism. In consequence, it is necessary to conduct the treatment with the patient being located in the vicinity of the photocoagulator. In addition, the manipulation of the arm mechanism is complicated. For these reasons, it is very difficult for the oculist to make the remedy without the help of a skilled assistant.

The combination of the slitlamp and the contact lens can suitably be used and are widely available for the operation in the region near the center of the fundas oculi, because it permits an easy photocoagulation operation and a fine coagulation. This type of ophthalmoscope, however, requires the patient to take sendentary posture during operation and can hardly be applied to the patient in the supination posture. For this reason, the combination of the slitlamp and the contact lens can hardly be applied to the treatment when the patient has the lesion in the peripheral portion of the fundus oculi.

SUMMARY OF THE INVENTION

Accordingly, an object of the invention is to provide a photocoagulator having a wider field of vision, as well as greater degree of freedom of operation, and capable of facilitating the remedy of lesion in the peripheral portion of the fundus oculi.

To this end, according to the invention, there is provided a photocoagulator comprising a main body including a light source means, an opthalmoscope carried by the head, etc. of an operator means and an optical fiber means for introducing the light beam from the light source means to the ophthalmoscope means.

According to the specific form of the present invention the photocoagulator is provided such that the optical beam path from the laser beam oscillator may be switched with the use of a Penta prism between two optical fibers one of which transmits the laser beam to an opthalmoscope and the other one of which transmits the laser beam to a slit lamp so that the treatment of photocoagulation can be suitably made in accordance with positions of a lesion to be treated on the patient's fundus oculi.

The above and other objects, as well as advantageous features of the invention will become more clear from the following description of the preferred embodiment taken in conjunction with the accompanying drawings.

BRIEF DESCRIPTION OF THE DRAWINGS

FIG. 1 is a schematic front elevational view of a photocoagulator constructed in accordance with an embodiment of the invention;

FIG. 2 is a plan view of the photocoagulator shown in FIG. 1;

DESCRIPTION OF THE PREFERRED EMBODIMENT

Figure 3:
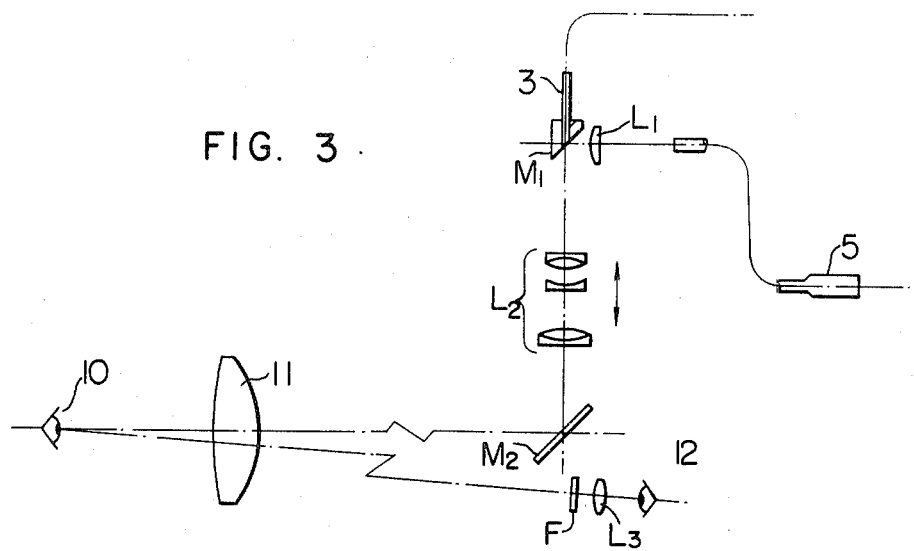
FIG. 3 is an illustration of an optic system incorporated in the embodiment shown in FIG. 1.

Referring first to FIG. 1 which is an elevational view of a first embodiment, a photocoagulator of the first embodiment has a laser device housing 1 encasing laser tube, a laser control system and so forth, a control box 2 for controlling various operation factors such as the intensity of illumination light, the intensity of coagulation light (laser beam), coagulation time and so on, an optical fiber device 3 for laser beam adapted to transmit a laser beam coming from a laser oscillator, an illumination light source 4, an optical fiber device 5 for transmitting the illumination light, a lens holder unit 6 accommodating therein a lens system for transmitting the laser beam and the illumination light to the patient's eye 10, a fastening band 7 for fastening the binocular indirect ophthalmoscope to the oculist's head, and a binocular magnifier 8 which is addapted to be rotated together with the lens holder unit 6 by means of a rotary shaft 9. The parts 4 to 9 mentioned hereinbefore constitute in combination a binocular indirect ophthalmoscope which is adapted to be carried on the oculist's head. The binocular indirect ophthalmoscope, however, may be carried by an arm supported by a universal joint. It is also possible to use a monocle indirect ophthalmoscope in place of the binocular indirect opthalmoscope. A reference numeral 11 designates an ophthalmoscope lens for magnifying the image of the fundas oculi of the patient's eye. This lens is usually an aspherical lens. A reference numeral 12 designates an oculist's eye.

Referring now to FIG. 3 showing an optical system of the photocoagulator of this embodiment, a focussing lens $L_1$ for the illumination light and a perforated mirror $M_1$ are arranged such that the optic axis of the laser beam is coincident with the optical axis of the illumination light. It is possible to use a half mirror or a dichroic mirror in place of the perforated mirror $M_1$. It is also possible to combine the optical fiber for the illumination light with the optical fiber for the coagulation light beam so that the latter is inserted into the central bore of the hollow optical fiber for the illumination light. The laser beam and the illumination light coaxial therewith are projected on the patient's eye by mean of a projection lens $L_2$. The size of the spot of the laser beam imaging on the fundus oculi is changed by moving the projection lens $L_2$ in the direction of optical axis A mirror $M_2$ is housed in the aforementioned lens holder unit 6 together with the aforementioned lens $L_1$ and the mirror $M_1$. A filter F for protecting the oculist's eye 12 is adapted to be placed out of the path of light during the observation and the sighting, but is moved into the path of light in advance to the coagulating operation thereby to protect the oculist's eye. A lens $L_3$ denotes an ocular for observing the patient's eye.

Figure 4:
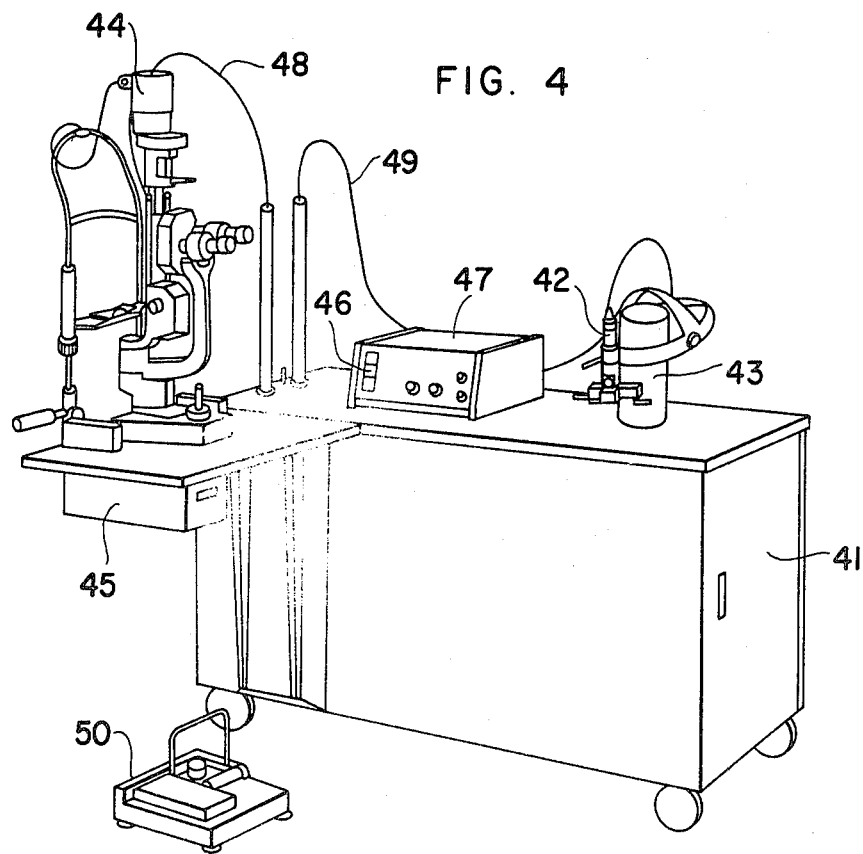
FIG. 4 is a schematic transparent illustration of a photocoagulator in accordance with a second embodiment of the invention.

FIG. 4 is a perspective illustration of a photocoagulator constructed in accordance with a second embodiment of the invention in which a slitlamp is combined with a binocular indirect ophthalmoscope for permitting a switching of the laser beam. A laser device housing 41 encases a laser tube, a laser control system and so forth. The binocular indirect ophthalmoscope 42 is mounted on a carrier 43, while a slitlamp 44 is adapted to be moved up and down by means of a slit table 45. A reference numeral 46 generally designates change-over switches, while a numeral 47 denotes a control box for controlling various factors of coagulation such as, for example, coagulation time, coagulation power and spot size and so forth of the laser beam. Optical fibers 48, 49 for the laser beam are connected to the binocular indirect ophthalmoscope 42, and to the slitlamp 44 respectively. A foot switch device 50 has two pedals: namely a pedal for triggering the optical coagulation and another pedal for triggering the vertical movement of the slit table 45.

Figure 5:
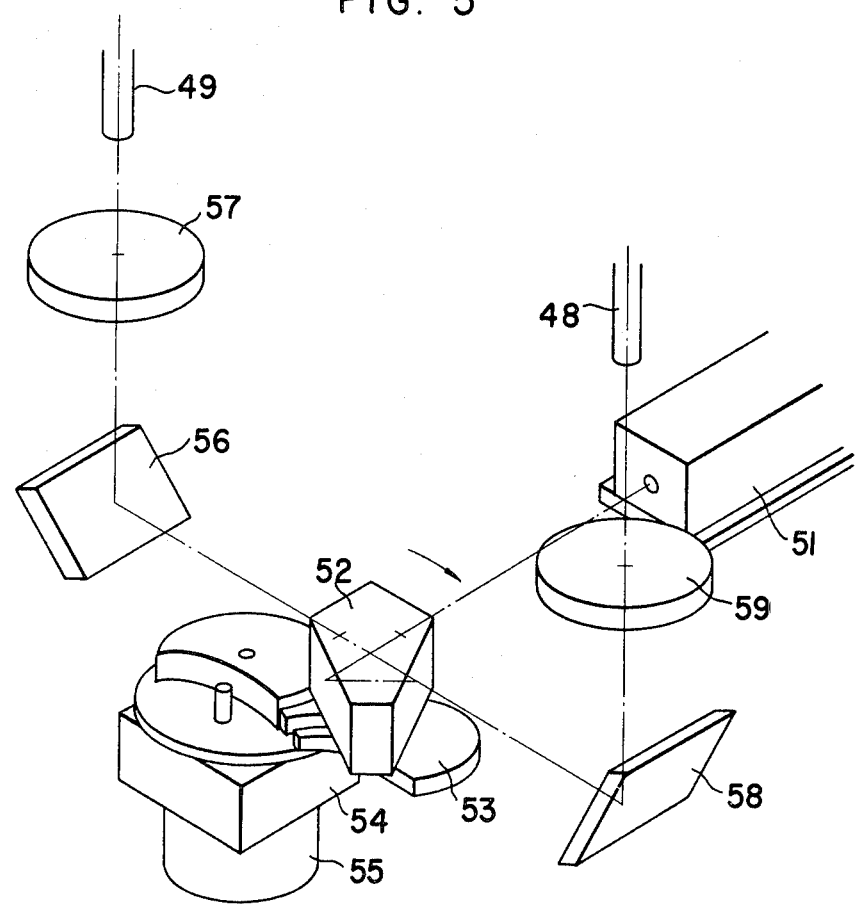
FIG. 5 is a transparent illustration of an optical system incorporated in the embodiment shown in FIG. 4.

Referring now to FIG. 5 illustrating the manner of switching of the path of laser beam from the laser oscillator, the arrangement for switching the path of the laser beam is accommodated in the laser device housing 41 shown in FIG. 4. A rotatable penta prism 52 is adapted to perpendicularly refelct the laser beam coming from the laser oscillator 51. The penta prism 52 is fixed to a Geneva mechanism 53 having a stop position at 90° interval. Reference numerals 54, 55 and 56 designate a gear head, D.C. motor and a mirror respectively. Numerals 57 and 59 denote condenser lenses, while 58 designates a mirror. The laser beam reflected by the penta prism 52 is transmitted to either one of the optical fibers 48, 49 for laser beams.

The photocoagulator of the invention having the construction described hereinbefore operates in a manner explained hereinunder. Referring back to FIGS. 1 to 3, the oculist with his head carrying the binocular indirect ophthalmoscope fastened by means of the belt 7 holds in his one hand the aspherical lens 11 and positions the latter in front of the patient's eye 10. In consequence, the laser sighting beam and the illumination light are applied to the fundas oculi of the patient's eye through the projection lens $L_2$, the mirror $M_2$ and the opthalmoscope lens 11. The laser sighting beam is applied to the fundus oculi through a light reducing filter which is not shown. The image reflected from the fundas oculi is magnified by the opthalmoscope lens 11 and is observed by means of the oculist's eye 12. The oculist moved around the patient in order to examine all portions of the fundus oculi. In some cases, the oculist strongly presses the sclera of the patient's eye to inspect and coagulate the peripheral portion of the fundus oculi. If any lesion is found out, the oculist manipulates the apparatus to aim at the thus found lesion with the sighting laser beam, and operates the foot switch (See FIG. 4) to turn on the trigger switch to apply the coagulation light beam thereby to cure the lesion on the fundus oculi. In advance to the operation, the light reducing filter is moved away from the path of light, while the protective filter is automatically moved into the path of light to protect the oculist's eye. Preferably, the foot switch is so constructed as to be movable following up the movement of the oculist.

In the apparatus shown in FIGS. 4 and 5, the laser beam emitted from the laser oscillator 51 can be reflected by the inner surfaces (mirror surfaces) of the penta prism 52 in two directions, and is applied in one of these directions to the end of the optical fiber 49 for the laser beam through the mirror 56 and the condenser lens 57. The other end of the optial fiber 49 for the laser beam is connected to the slitlamp 44 so that the oculist can conduct the operation by means of the slitlamp. A.D.C. motor 55 is started as the change-over switch 46 is manipulated, so that the penta prism 52 is rotated 90° in the direction of the arrow together with the Geneva mechanism 53. In consequence, the laser beam is reflected by the reflecting surface of the penta prism in the other one of the directions, and is applied to the end of the optical fiber 48 for laser beam through the mirror 58 and the condenser lens 59. The other end of the optical fiber 48 is connected to the binocular ophthalmoscope 42 so that the oculist can conduct the operation with the binocular opthalmoscope.

As will be understood from the foregoing description, the photocoagulator of the invention has a large flexibility of operation and, hence, can be applied even to a patient in the supination posture. In addition, a wide field of vision permits an easy inspection of the peripheral portion of the fundas oculi and makes it possible to effect the treatment even on the peripheral portion of the fundus oculi which is usually invisible due to pressing of the eyeball. Thus, the photocoagulator of the invention can effectively be used particularly for the remedy of the immature retinopathy, retinal detachment and so forth. Both of the laser beam and the illumination light are introduced by means of the optical fibers so that the indirect opthalmoscope portion is isolated from the light sources both electrically and thermally to ensure a high safety of the optical coagulator.

By switching the path of laser beam from a single laser device, it is possible to effect a fine coagulation by the slit lamp type method, when the remedy is to be made on the central region of the fundus oculi.

Although the invention has been described through specific terms, it is to be noted here that the described embodiment are not exclusive and various changes and modifications may be imparted thereto without departing from the scope of the invention which is limited solely by the appended claims.

What is claimed is:

1. A photocoagulator including an opthalmoscope and a slit lamp, both of which are adapted to direct a laser beam and illumination light to a lesion on a patient's fundus oculi comprising:
   i. means for producing a laser beam;
   ii. first fiber means for guiding said laser beam to said opthalmoscope;
   iii. second fiber means for guiding said laser beam to said slit lamp;
   iv. means for switching said laser beam from said laser beam producing means so as to direct the laser beam to said first or second fiber, selectively, said switching means including a penta prism for refracting and reflecting said laser beam from said laser beam producing means, and means for controlling the position of said penta prism so that said laser beam from said laser beam producing means is selectively directed to said first or second fiber means through a penta prism;
   whereby the treatment of photocoagulation can be suitably made in accordance with positions of a lesion on the patient's fundus oculi.

2. A photocoagulator as set forth in claim 1, wherein said opthalmoscope is a binocular indirect opthalmoscope.

3. A photocoagulator as set forth in claim 1, wherein said opthalmoscope is a monocle indirect opthalmoscope.

4. A photocoagulator as set forth in claim 1, wherein said control means for the position of said penta prism comprises means for switching the position of said penta prism so that said prism is rotated to an angle of 90 degrees.

* * * * *